United States Patent [19]

Jäger et al.

[11] 4,006,008

[45] Feb. 1, 1977

[54] 1-ALKYLIDENEAMINOURACIL COMPOUNDS AND HERBICIDAL COMPOSITIONS

[75] Inventors: Gerhard Jäger; Jürgen Wenzelburger, both of Wuppertal; Ludwig Eue; Robert Rudolf Schmidt, both of Cologne, all of Germany

[73] Assignee: Bayer Aktiengesellschaft, Leverkusen, Germany

[22] Filed: Jan. 14, 1974

[21] Appl. No.: 433,165

[30] Foreign Application Priority Data

Jan. 16, 1973 Germany .......................... 2301971

[52] U.S. Cl. ........................................ 71/88; 71/90; 71/92; 260/240 G; 260/256.4 Q; 260/256.4 C; 260/256.5 R

[51] Int. Cl.² ...................... A01N 9/22; A01N 9/12

[58] Field of Search ............ 260/256.4 C, 256.5 R, 260/240 G; 71/88, 90, 92

[56] References Cited

OTHER PUBLICATIONS

Kloetzer, et al., "Chemical Abstracts," vol. 65, 1966, col. 13700g.

Kloetzer, et al., "Chemical Abstracts," vol. 66, 1967, col. 46390t.

Kato, et al., "Chemical Abstracts," vol. 74, 1971, col. 53718z.

*Primary Examiner*—R. Gallagher
*Assistant Examiner*—James H. Turnipseed
*Attorney, Agent, or Firm*—Burgess, Dinklage & Sprung

[57] ABSTRACT

Novel 1-alkylideneaminouracil compounds of the formula

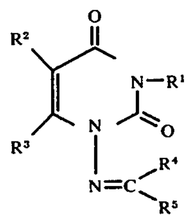

(I)

in which $R^1$ is optionally substituted hydrocarbyl which may contain hetero-atoms.

$R^2$ is hydrogen or halogen; and $R^3$ is hydrogen or alkyl; or $R^2$ and $R^3$ together represent a multi-membered methylene bridge which forms, with the two carbon atoms in the 5- and 6-position of the heterocyclic structure, a fused ring which is optionally substituted by alkyl.

$R^4$ is alkyl, cycloalkyl, cycloalkenyl, optionally substituted 5-membered or 6-membered heteroaryl with the hetero-atoms O, N or S; and $R^5$ is hydrogen, alkyl or optionally substituted aryl; advantageously employ the selective herbicides in crops, e.g., in cotton or cereal crops.

42 Claims, No Drawings

1-ALKYLIDENEAMINOURACIL COMPOUNDS AND HERBICIDAL COMPOSITIONS

The present invention relates to certain new 1-alkylideneaminouracil compounds, to herbicidal compositions containing them and to their use as herbicides.

It is known from U.S. Pat. Nos. 3,005,015 and 3,235,357 that 3-cyclohexyl-5,6-trimethyleneuracil possesses herbicidal properties. However, its action is not always entirely satisfactory when it is employed as a selective weed-killer in cereals (including corn) and cotton, especially if small amounts and low concentrations are used.

The present invention provides 1-alkylideneaminouracils of the formula

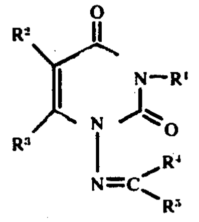

(I)

in which $R^1$ is alkyl which is optionally substituted by halogen, nitrile or alkoxy, or represents alkenyl, alkynyl, cycloalkyl, alkylcycloalkyl, cycloalkylalkyl, halocycloalkyl, alkoxycarbonylalkyl, alkylthioalkyl, alkoxyalkyl or aralkyl which is optionally substituted in the aryl part.

$R^2$ is hydrogen or halogen; and $R^3$ is hydrogen or alkyl; or $R^2$ and $R^3$ together represent a multi-membered methylene bridge which forms, with the two carbon atoms in the 5- and 6-positions of the heterocyclic structure, a fused ring which is optionally substituted by alkyl.

$R^4$ is alkyl, cycloalkyl, cycloalkenyl, optionally substituted 5-membered or 6-membered heteroaryl with the hetero-atoms O, N or S; and $R^5$ is hydrogen, alkyl or optionally substituted aryl.

Preferably, $R^1$ is straight-chain or branched alkyl of from 1 to 12 carbon atoms which is optionally substituted by halogen, nitrile or alkoxy of from 1 to 3 carbon atoms, or $R^1$ is straight-chain or branched alkenyl or alkynyl of from 3 to 12 carbon atoms, cycloalkyl of from 5 to 7 carbon atoms, cycloalkylalkyl of from 5 to 8 carbon atoms (especially of 6 carbon atoms in the cycloalkyl part and 1 to 2 carbon atoms in the alkyl part) or alkylcycloalkyl of from 5 to 8 carbon atoms in the cycloalkyl part, which can be substituted by alkyl of from 1 to 3 carbon atoms (especially methyl), or $R^1$ is aralkyl of from 6 to 10 (preferably 6) carbon atoms in the aryl part and 1 or 2 carbon atoms in the alkyl part, which is optionally substituted in the aryl part (preferred substituents are halogen, especially chlorine, haloalkyl of from 2 to 5 halogen atoms, especially fluorine, and 1 or 2 carbon atoms, and straight-chain or branched alkyl of from 1 to 4 carbon atoms, especially methyl), or $R^1$ is alkoxyalkyl or alkylthioalkyl of from 1 to 4 carbon atoms in the alkoxy or alkylthio part and 1 to 6 carbon atoms in the alkyl part, or alkoxycarbonylalkyl of from 1 to 4 carbon atoms in the alkoxy part and 1 or 2 carbon atoms in the alkyl part; $R^2$ is hydrogen, chlorine or bromine, and $R^3$ is hydrogen or alkyl of from 1 to 4 carbon atoms (especially methyl), or $R^2$ and $R^3$ together represent a straight-chain or branched methylene bridge of from 3 to 5 members, which forms, with the two adjacent carbon atoms, a 5-membered to 7-membered ring which is optionally substituted by alkyl of from 1 to 3 carbon atoms (especially methyl); $R^4$ is straight-chain or branched alkyl of from 1 to 6 carbon atoms (for example methyl or ethyl), or $R^4$ is cycloalkyl or cycloalkenyl of from 5 to 7 carbon atoms (for example cyclohexyl or cyclohex-3-enyl) or aryl of from 6 to 10 carbon atoms (especially of 6 carbon atoms) which is optionally substituted one to three times (for example by halogen, especially chlorine, haloalkyl or haloalkoxy of 1 or 2 carbon atoms and 2 to 5 halogen atoms, especially fluorine, straight-chain or branched alkyl of from 1 to 4 carbon atoms, especially of 1 or 2 carbon atoms, alkoxy, alkylthio or alkylsulfonyl of from 1 to 3 carbon atoms in the alkyl or alkoxy part, hydroxyl and nitro), or $R^4$ is 5-membered or 6-membered heteroaryl with O, N or S as hetero-atoms, which are optionally mono-substituted or polysubstituted by any of the above-mentioned substituents for aryl (so that $R^4$ can be, for example, 2-furyl, 3-furyl, 2-pyridinyl, 3-pyridinyl, 4-pyridinyl, 2-pyrimidinyl, 3-pyrimidinyl, 4-pyrimidinyl, 2-thienyl, 2-thiazolyl-(1,3), 5-thiazolyl-(1,3), 2-thiadiazolyl-(1,3,4) or 5-thiadiazolyl-(1,3,4)); and $R^5$ is hydrogen, alkyl of from 1 to 6 (especially of from 1 to 4) carbon atoms, or aryl of from 6 to 10 carbon atoms (especially of 6 carbon atoms) which is optionally substituted one to three times, for example by any of the substituents just mentioned for aryl).

The invention also provides a process for the preparation of a 1-alkylideneaminouracil of the formula (I) in which a 1-aminouracil of the formula

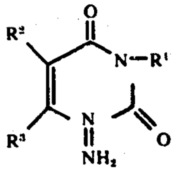

(II)

in which $R^1$, $R^2$ and $R^3$ have the above-mentioned meanings, is reacted with an aldehyde or ketone of the formula

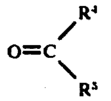

(III)

in which $R^4$ and $R^5$ have the above-mentioned meanings, either in the presence of an aliphatic carboxylic acid and optionally in the presence of an organic inert solvent (process variant (a)) or in the presence of an organic polar solvent and optionally in the presence of an acid catalyst (process variant (b)).

Surprisingly, the 1-alkylideneaminouracils according to the invention display a substantially better selective activity in crops such as cereals (including corn) and cotton, together with better herbicidal potency, than 3-cyclohexyl-5,6-trimethyleneuracil, which is chemically the nearest active compound of the same type of action. The new active compounds according to the invention thus represent an enrichment of the art.

If 1-amino-3-cyclohexyl-5,6-trimethyleneuracil and benzaldehyde are used as starting compounds, the course of the reaction can be represented by the following formula scheme:

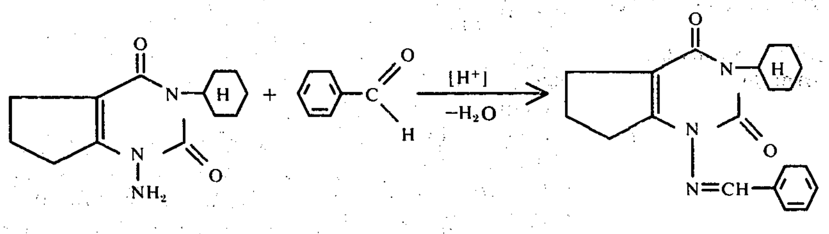

The formula (II) provides a general definition of the 1-aminouracils used as starting compounds.

The following may be mentioned individually as examples of the 1-aminouracils of formula (II): 1-amino-3-cyclohexyl-5-bromo-6-methyl-uracil, 1-amino-3-cyclohexyl-6-methyl-uracil, 1-amino-3-benzyl-6-methyl-uracil, 1-amino-3-sec.-butyl-5-bromo-6-methyl-uracil, 1-amino-3-isopropyl-6-methyl-uracil, 1-amino-3-isopropyl-5-bromo-6-methyl-uracil, 1-amino-3-n-butyl-6-methyl-uracil, 1-amino-3-o-methylcyclohexyl-5-bromo-6-methyl-uracil, 1-amino-3-cyclohexyl-5,6-trimethylene-uracil, 1-amino-3-cycloheptyl-5,6-trimethylene-uracil, 1-amino-3-cyclooctyl-5,6-trimethylene-uracil, 1-amino-3-(4-methylcyclohexyl)-5,6-trimethylene-uracil, 1-amino-3-(3,5,5-trimethylcyclohexyl)-5,6-trimethylene-uracil, 1-amino-3-cyclohexylmethyl-5,6-trimethylene-uracil, 1-amino-3-ethyl-5,6-trimethylene-uracil, 1-amino-3-propyl-5,6-trimethylene-uracil, 1-amino-3-isopropyl-5,6-trimethylene-uracil, 1-amino-3-butyl-5,6-trimethylene-uracil, 1-amino-3-isobutyl-5,6-trimethylene-uracil, 1-amino-3-sec.-butyl-5,6-trimethylene-uracil, 1-amino-3-chloroethyl-5,6-trimethylene-uracil, 1-amino-3-dodecyl-5,6-trimethylene-uracil, 1-amino-3-allyl-5,6-trimethylene-uracil, 1-amino-3-benzyl-5,6-trimethylene-uracil, 1-amino-3-(2-methyl)benzyl-5,6-trimethylene-uracil and 1-amino-(4-chlorobenzyl)-5,6-trimethylene-uracil.

The 1-aminouracils of the formula (II) have not previously been known; they form the subject of a separate patent application (compare German patent application No. P 22 07 549 (Le A 14 205). They can be prepared by A. reacting 2,3-dihydro-1,3-oxazine-2,4-diones of the formula

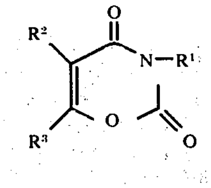
(IV)

in which $R^1$, $R^2$ and $R^3$ have the above-mentioned meanings with hydrazine, optionally in the presence of a diluent, at temperatures from −30° to +100° C, or B. reacting 1-aminouracils of the formula

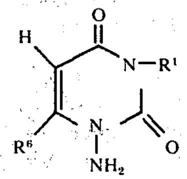
(IIA)

in which $R^1$ has the above-mentioned meaning; and $R^2$ is alkyl with halogen, especially bromine, optionally in the presence of an acid-binding agent and optionally in the presence of a solvent or diluent, at temperatures from 0° to 50° C (see preparative Examples below).

The 2,3-dihydro-1,3-oxazine-2,4-diones of the formula (IV) used as starting compounds, are known (see J. Chem. Soc. 1954, London, 845–849; Deutsche Offenlegungsschriften (German Published Specifications) Nos. 2,005,118 and 1,957,321; see Examples).

The formula (III) provides a general definition of the aldehydes and ketones used as staring compounds.

The following may be mentioned individually as examples thereof; benzaldehyde, 4-chlorobenzaldehyde, 3-chlorobenzaldehyde, 2,6-dichlorobenzaldehyde, 3,4-dichlorobenzaldehyde, 2-hydroxybenzaldehyde, 3-nitrobenzaldehyde, 3-trifluoromethylbenzaldehyde, 4-methoxybenzaldehyde, 4-tertiary butylbenzaldehyde, formylcyclohexane, 3,4-tetrahydrobenzaldehyde, formylcycloheptane, formylcyclopentane, acetaldehyde, chloral, n-propionaldehyde, n-butyraldehyde, isobutyraldehyde, n-valeraldehyde, isovaleraldehyde, n-capronaldehyde, furfuraldehyde, 2-pyrimidinaldehyde, acetone, methyl ethyl ketone, methyl n-propyl ketone, diethyl ketone, pinacoline and benzophenone.

The aldehydes or ketones of the formula (III) used as starting compounds are known.

Possible diluents in process variant (a) are aliphatic carboxylic acids, such as acetic acid. An inert organic solvent can, if appropriate, be employed additionally (because of the better solubility of the starting compounds oxazine and aldehyde or ketone). In this context, chlorinated hydrocarbons, such as methylene or chloroform, should especially be mentioned.

The reaction temperatures can be varied within a wide range in this variant. In general, temperatures from 10° to 80° C, preferably 15° to 40° C, are used.

In carrying out process variant (a), 1 to 1.5, preferably 1 to about 1.1, mols of aldehyde or ketone of the formula (III) are generally employed per mol of 1-aminouracil of the formula (II). The uracil, either in bulk or dissolved in a small amount of the above-mentioned organic solvent, may be introduced into the carboxylic acid and the aldehyde or the ketone, optionally also as a solution, may be added. After standing for approximately twelve hours at room temperature, the crystalline precipitate may be filtered off, washed with a little ether and dried. It can be purified by recrystallization, if desired.

Possible diluents in process variant (b) are organic polar solvents which can be distilled azeotropically with water. Preferred examples include hydrocarbons, such as benzene, toluene or xylene, or alcohols, such as ethyl alcohol or butanol.

The reaction in process variant (b) is optionally carried out with the aid of an acid catalyst. Preferred catalysts include inorganic monobasic or polybasic acids, such as hydrogen halides, sulfuric acid, phosphoric acid or perchloric acid or aliphatic carboxylic acids, such as trifluoroacetic acid or acetic acid.

The reaction temperatures can be varied over a wide range in variant (b). In general, a temperature from 50° to 150° C, preferably 80° to 130° C, is used.

In carrying out process variant (b), about 1 to 1.5, preferably 1 to 1.1, mols of aldehyde or ketone of the formula (III) (and 0.001 to 0.01 mol of catalyst if used) are employed per mol of 1-aminouracil of the formula (II). The uracil and aldehyde or ketone may be dissolved in the solvent, the catalyst may be added and the mixture heated for several hours under a water separator. After distilling off the solvent, the residue may be purified by recrystallization.

The following examples are illustrative of the preparation of the instant compounds:

EXAMPLE 1

Preparation of 1-furfurylideneamino-3-cyclohexyl-5,6-trimethyleneuracil

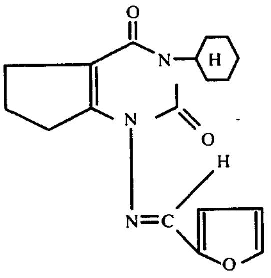

(1)

(according to process variant (a)):

5.8 g (0.06 mol) of furfuraldehyde were added to a solution of 12.5 g (0.05 mol) of 1-amino-3-cyclohexyl-5,6-trimethylene-uracil in 75 ml of glacial acetic acid. After standing for twelve hours at room temperature, the crystalline precipitate was filtered off and rinsed with a little cold ether.

After drying in vacuo over potassium hydroxide, 12.2 g (74.5% of theory) of 1-furfurylideneamino-3-cyclohexyl-5,6-trimethyleneuracil of melting point 169° - 170° was obtained.

EXAMPLE 2

Preparation of 1-(3,4-tetrahydrobenzylidene)-amino-3-cyclohexylmethyl-5,6-trimethyleneuracil

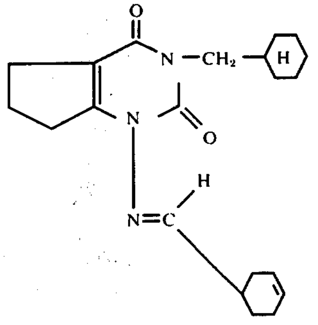

(2)

(according to process variant (b)):

A solution of 13.2 g (0.05 mol) of 1-amino-3-cyclohexylmethyl-5,6-trimethyleneuracil and 8.3 g (0.075 mol) of 3,4-tetrahydrobenzaldehyde in 100 ml of anhydrous benzene was heated, with one drop of concentrated sulfuric acid, for five hours to the boil while continuously separating off water. The solvent was then distilled off in vacuo and the oily residue obtained was recrystallized from petroleum ether.

13.4 g (75.5% of theory) of 1-(3,4-tetrahydrobenzylidene)-amino-3-cyclohexylmethyl-5,6-trimethyleneuracil of melting point 82°–83° C was obtained.

EXAMPLE 3

Preparation of 1-(3,4-dichlorobenzylideneamino)-3-cyclohexyl-5-bromo-6-methyl-uracil

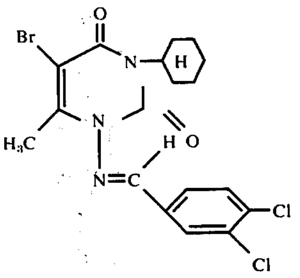

(3)

(according to variant (a)):

22.7 g (0.0753 mol) of 1-amino-3-cyclohexyl-5-bromo-6-methyl-uracil were dissolved in a mixture of 40 ml of dichloromethane and 150 ml of glacial acetic acid and 14 g (0.08 mol) of 3,4-dichlorobenzaldehyde were added thereto. After standing for twelve hours at room temperature, a crystalline precipitate was obtained, which was filtered off, rinsed with a little ether and dried over potassium hydroxide in vacuo (yield 18.8 g). The yield can be increased by concentration of the mother liquor and further working up as described.

31.3 g (90.5% of theory) of 1-(3,4-dichlorobenzylideneamino)-3-cyclohexyl-5-bromo-6-methyl-uracil of melting point 188°–189° C were obtained.

The active compounds listed in Table I which follows can be prepared analogously:

Table I
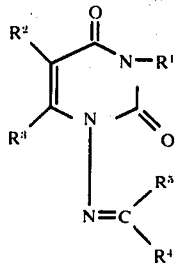
| No. | $R^1$ | $R^2$ | $R^3$ | $R^4$ | $R^5$ | Melting point, ° C |
|---|---|---|---|---|---|---|
| 4 | 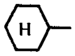 | H | $CH_3$ | 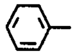 | H | 156–157 |
| 5 | 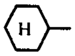 | Br | $CH_3$ | 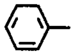 | H | 156 |
| 6 | 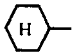 | Br | $CH_3$ | 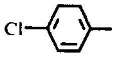 | H | 190–191 |
| 7 | 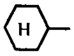 | Br | $CH_3$ | 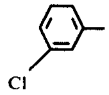 | H | 135–137 |
| 8 | 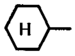 | Br | $CH_3$ | 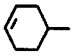 | H | 138–139 |
| 9 | 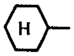 | Br | $CH_3$ | $CH_3$ | $CH_3$ | oil |
| 10 | 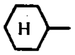 | H | $CH_3$ | $CH_3$ | $CH_3$ | 182 |
| 11 | $C_2H_5$ | $-(CH_2)_3-$ | | 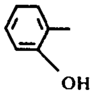 | H | 184–185 |
| 12 | $(CH_3)_2CH$ | $-(CH_2)_3-$ | | 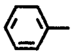 | H | 169 |
| 13 | $(CH_3)_2CH$ | $-(CH_2)_3-$ | | 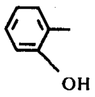 | H | 230–231 |
| 14 | $(CH_3)_2CHCH_2$ | $-(CH_2)_3-$ | | 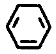 | H | 127–128 |
| 15 | $(CH_3)_2CHCH_2$ | $-(CH_2)_3-$ | | 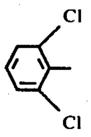 | H | 140–141.5 |
| 16 | $(CH_3)_2CHCH_2$ | $-(CH_2)_3-$ | | $CH_3$ | $CH_3$ | 114–115 |
| 17 | $ClC_2H_4$ | $-(CH_2)_3-$ | | 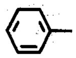 | H | 152–154 |
| 18 | $ClC_2H_4$ | $-(CH_2)_3-$ | | 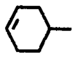 | H | 74–75.5 |
| 19 | $ClC_2H_4$ | $-(CH_2)_3-$ | | 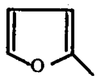 | H | 140–141 |

Table I-continued
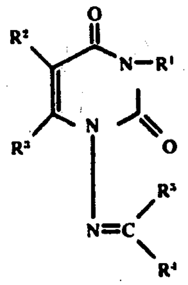
| No. | $R^1$ | $R^2$ | $R^3$ | $R^4$ | $R^5$ | Melting point, °C |
|---|---|---|---|---|---|---|
| 20 | $CH_2{=}CH{-}CH_2$ | $-(CH_2)_3-$ | | 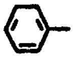 | H | 105–107 |
| 21 | $CH_3-(CH_2)_{11}$ | $-(CH_2)_3$ | | 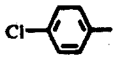 | H | 67–69 |
| 22 | 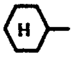 | $-(CH_2)_3-$ | | $CH_3$ | $CH_3$ | 106–107 |
| 23 | 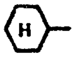 | $-(CH_2)_3-$ | | 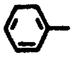 | H | 194–195 |
| 24 | 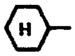 | $-(CH_2)_3-$ | | 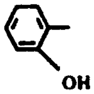 | H | 240–242 |
| 25 | 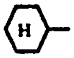 | $-(CH_2)_3-$ | | 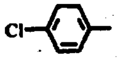 | H | 218–220 |
| 26 | 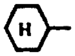 | $-(CH_2)_3-$ | | 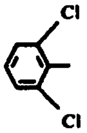 | H | 191–192.5 |
| 27 | 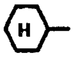 | $-(CH_2)_3-$ | | 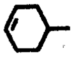 | H | 82–83 |
| 28 | 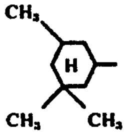 | $-(CH_2)_3-$ | | 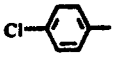 | H | 156–157 |
| 29 | 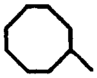 | $-(CH_2)_3-$ | | 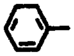 | H | 172–173 |
| 30 | 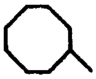 | $-(CH_2)_3-$ | | 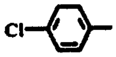 | H | 211–212 |
| 31 | 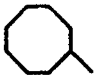 | $-(CH_2)_3-$ | | 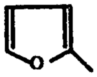 | H | 178–179 |
| 32 | 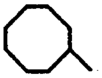 | $-(CH_2)_3-$ | | 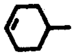 | H | 88–89 |
| 33 | 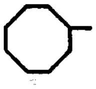 | $-(CH_2)_3-$ | | 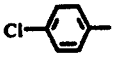 | H | 230.5–232 |

Table I-continued
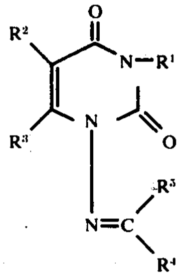
| No. | $R^1$ | $R^2$ | $R^3$ | $R^4$ | $R^5$ | Melting point, ° C |
|---|---|---|---|---|---|---|
| 34 | 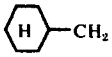 | $-(CH_2)_3-$ | | 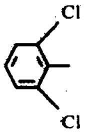 | H | 182.5–183 |
| 35 | 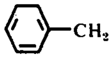 | $-(CH_2)_3-$ | | 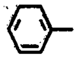 | H | 176–177 |
| 36 | 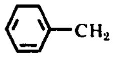 | $-(CH_2)_3-$ | | 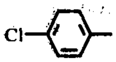 | H | 177–178 |
| 37 | 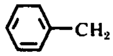 | $-(CH_2)_3-$ | | 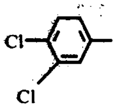 | H. | 187–188.5 |
| 38 | 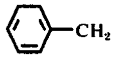 | $-(CH_2)_3-$ | | 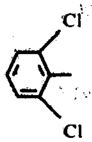 | H | 193–194 |
| 39 | 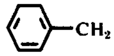 | $-(CH_2)_3-$ | | 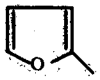 | H | 167.5–169 |
| 40 | 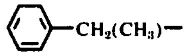 | $-(CH_2)_3-$ | | 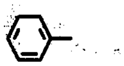 | H | 174.5–175.5 |
| 41 | 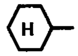 | Br | $CH_3$ | 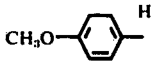 | H | 148–149 |
| 42 | 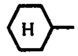 | Br | $CH_3$ | 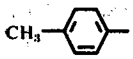 | H | 185–186 |
| 43 | 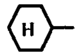 | Br | $CH_3$ | 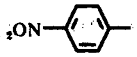 | H | 209–210 |
| 44 | 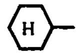 | Br | $CH_3$ | 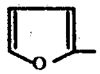 | H | 143–144 |
| 45 | 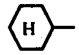 | Cl | $CH_3$ | 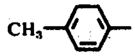 | H | 186–187 |
| 46 | 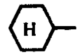 | Cl | $CH_3$ | 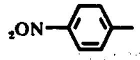 | H | 198–199 |
| 47 | 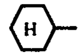 | Cl | $CH_3$ | 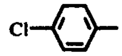 | H | 179–181 |

Table I-continued

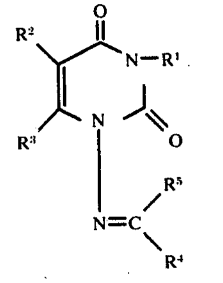

| No. | $R^1$ | $R^2$ | $R^3$ | $R^4$ | $R^5$ | Melting point, ° C |
|---|---|---|---|---|---|---|
| 48 | 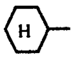 | Cl | $CH_3$ | 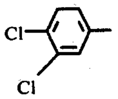 | H | 174–175.5 |
| 49 | 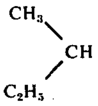 | Br | $CH_3$ | 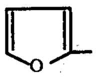 | H | 131.5–132.5 |
| 50 | 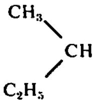 | Cl | $CH_3$ | 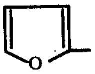 | H | 132–133 |
| 51 | 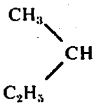 | Br | $CH_3$ | 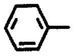 | H | 119–120 |
| 52 | 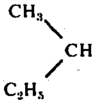 | Cl | $CH_3$ | 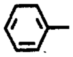 | H | 91–92 |
| 53 | 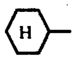 | Cl | $CH_3$ | 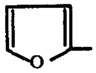 | H | 137–139 |
| 54 | 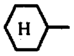 | Cl | $CH_3$ | 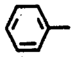 | H | 156.5–157.5 |

Examples of the 1-aminouracils of the formula (II) to be used as starting compounds:

A. 1-amino-3-cyclohexyl-5,6-trimethylene-uracil

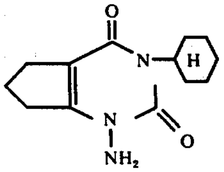

A solution of 30 ml (0.6 mol) of hydrazine hydrate in 30 ml of dimethylformamide was added dropwise, while stirring, to a solution of 23.5 g (0.1 mol) of 3-cyclohexyl-2,3,4,5,6,7-hexahydro-cyclopenta[e]-1,3-oxazinedione-(2,4) in 30 ml of dimethylformamide at a temperature of −2° to +6° C and the reaction mixture was stirred for 12 hours at +6° C. 800 ml of water was added while stirring and the resulting precipitate was filtered off, washed with water and dried over phosphorous pentoxide.

17 g (70% of theory) of 1-amino-3-cyclohexyl-5,6-trimethylene-uracil of melting point 149°–150° C were obtained.

The oxazinedione derivative of the formula

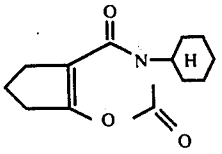

required for the synthesis can be prepared as follows:

732 g (4 mols) of adipic acid dichloride were added dropwise over the course of 45 minutes to a solution, warmed to 120° C, of 751.2 g (6 mols) of cyclohexylisocyanate and 648 ml (8 mols) of pyridine in 1.5 l of xylene, while stirring well and applying reflux cooling. After stirring for three hours at 120° C, the reaction mixture was cooled to 10° C, the pyridine hydrochloride which had separated out was filtered off and the precipitate was twice rinsed with 200 ml of xylene at a time. The filtrate was freed of the solvent under reduced pressure until dryness was reached, the residue was boiled up with 4 l of ligroin, the mixture was filtered and the filtrate was concentrated. On cooling, a precipitate was obtained, which was dissolved in 75% strength aqueous methanol, the solution was cooled to 0° C, and the product was precipitated by adding water.

810 g (86.5% of theory) of 3-cyclohexyl-2,3,4,5,6,7-hexahydro-cyclopenta[e]-1,3-oxazine-2,4-dione of melting point 72° to 74° C were obtained. The produce was sufficiently pure for further conversion. The melting point rose to 81° – 82° C on recrystallizing a sample from ligroin.

B. 1-amino-hexahydrobenzyl-5,6-trimethylene-uracil

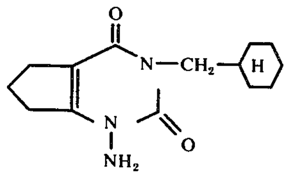

A solution of 150 ml of hydrazine hydrate in 100 ml of dimethylformamide was added dropwise to a solution of 168.8 g (0.68 mol) of 3-hexahydrobenzyl-5,6-trimethylene-2,3-dihydro-1,3-oxazinedione-(2,4) in 200 ml of dimethylformamide at 0° to 10° C. Thereafter the mixture was stirred for a further 24 hours at 20° – 25° C and the crystals which had separated out were filtered off, rinsed with a little dimethylformamide and ether and dried in vacuo. 136.5 g (76.4% of theory) of 1-amino-3-hexahydrobenzyl-5,6-trimethylene-uracil of melting point 137° C were obtained.

The oxazinedione derivative required for this synthesis can be prepared, analogously to the description under (A), from adipic acid dichloride and hexahydrobenzylisocyanate.

The new 1-alkylideneaminouracils according to the invention have very good herbicidal properties and can therefore be used for combating weeds.

Weeds in the broadest sense are plants which grow in positions where they are not desired: as weeds there may be mentioned: dicotyledons such as mustard (Sinapis), cress (Lepidium), cleavers (Galium), chickweed (Stellaria), camomile (Matricaria), gallant soldier (Galinsoga), goosefoot (Chenopodium), annual nettle (Urtica), groundsel (Senecio) and monocotyledons, such as timothy (Phleum), blue grass (Poa), fescur (Festuca), goosegrass (Eleusine), foxtail (Setaria), ryegrass (Lolium) and barnyard grass (Echinochloa).

The active compounds according to the invention have a very strong influence on plant growth but in different ways, so that they can be used as selective herbicides.

The active compounds according to the invention are distinguished by good selective herbicidal activity. Thus, it is possible to employ them as selective agents for combating weeds in crop plantings such as cereals (including corn) and cotton.

The active compounds according to the present invention can be converted into the usual formulations, such as solutions, emulsions, suspensions, powders, pastes and granulates. These may be produced in known manner, for example, by mixing the active compounds with extenders, that is, liquid or solid or liquefied gaseous diluents or carriers, optionally with the use of surface-active agents, that is, emulsifying agents and/or dispersing agents, and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil franctions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, e.g. aerosol propellants, such as halogenated hydrocarbons, e.g. freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates, as well as albumin hydrolyzation products; and preferred examples of dispersing agents include lignin, sulfite waste liquors and methyl cellulose.

The active compounds according to the invention can be used as a mixture with other active compounds.

The formulations in general contain from 0.1 to 95 per cent by weight of active compound, preferably 0.5 to 90.

The active compounds can be employed as such or in the form of their formulations or the use forms prepared therefrom, such as ready-to-use solutions, emulsions, suspensions, powders, pastes and granules. They may be applied in the usual manner, for example by watering, spraying, atomizing, sprinkling or dusting.

They can be applied both according to the post-emergence method and according to the pre-emergence method; they are preferably used after the plants have emerged.

The amount of active compound employed can vary within wide ranges. It essentially depends on the nature of the desired effect. In general, the amounts used are from 0.1 to 25 kg/ha, preferably 0.5 to 10 kg/ha.

The invention therefore provides a herbicidal composition containing as active ingredient a compound according to the invention in admixture with a solid or liquefied gaseous diluent or carrier or in admixture with a liquid diluent or carrier containing a surface-active agent.

The invention also provides a method of combating weeds which comprises applying to the weeds or their habitat a compound according to the invention alone or in the form of a composition containing as active ingredient a compound according to the invention in admixture with a diluent or carrier. The invention also provides methods of obtaining crops protected from damage by weeds by being grown in areas in which, immediately prior to and/or during the time of the growing, a compound according to the invention was applied alone or in admixture with a diluent or carrier. It will be seen that the usual methods of providing a harvested crop may be improved by the present invention.

The compounds according to the invention, and the preparation and use of the compounds according to the invention, are illustrated by the following Examples.

EXAMPLE A

Pre-emergence test

Solvent: 5 parts by weight of acetone

Emulsifier: 1 part by weight of alkylaryl polyglycol ether

To produce a suitable preparation of active compound, 1 part by weight of active compound was mixed with the stated amount of solvent, the stated amount of emulsifier was added and the concentrate was then diluted with water to the desired concentration.

Seeds of the test plants were sown in normal soil and, after twenty-four hours, watered with the preparation of the active compound. It was expedient to keep constant the amount of water per unit area. The concentration of the active compound in the preparation was of no importance, only the amount of active compound applied per unit area being decisive. After three weeks, the degree of damage to the test plants was determined and characterized by the values 0–5, which had the following meaning:

0—no effect
1—slight damage or delay in growth
2—marked damage or inhibition of growth
3—heavy damage and only deficient development or only 50% emerged
4—plants partially destroyed after germination or only 25% emerged
5—plants completely dead or not emerged.

The active compounds, the amounts applied and the results obtained can be seen from the following Table:

Table II

Pre-emergence Test

| Active compound | Amount of active compound used, kg/ha pis | Sina- ria | Stella- soga | Galin- caria | Matri- oats | ton | Cot- wheat | corn | |
|---|---|---|---|---|---|---|---|---|---|
| 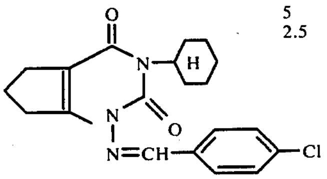 | 5 | 2 | 4–5 | 4–5 | 5 | 2 | O | 2 | 0 |
| | 2.5 | 2 | 4–5 | 4–5 | 4–5 | 1 | 0 | 1 | 0 |
| 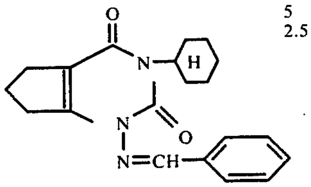 | 5 | 4 | 5 | 5 | 5 | 3 | 0 | 2 | 0 |
| | 2.5 | 3 | 5 | 5 | 5 | 3 | 0 | 1 | 0 |
| 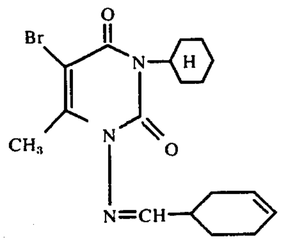 | 5 | 5 | 5 | 4–5 | 4–5 | 1 | 2 | 3 | 1 |
| | 2.5 | 5 | 4–5 | 4–5 | 4 | 0 | 1 | 3 | 1 |
| 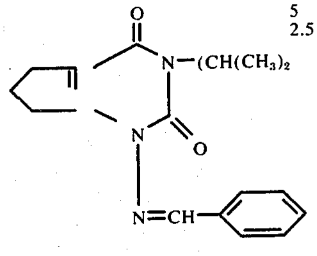 | 5 | 3 | 5 | 5 | 5 | 2 | 1 | 0 | 1 |
| | 2.5 | 2 | 4–5 | 4–5 | 4 | 1 | 1 | 0 | 0 |

Table II-continued

| Pre-emergence Test | | | | | | | | | |
|---|---|---|---|---|---|---|---|---|---|
| Active compound | Amount of active compound used, kg/ha pis | Sina-ria | Stella-soga | Galin-caria | Matri-oats | ton | Cot-wheat | corn | |
| 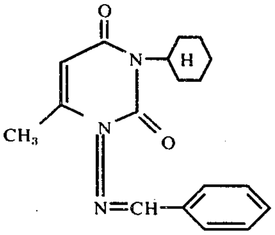 | 5 | 4–5 | 5 | 5 | 5 | 3 | 1 | 3 | 1 |
| | 2.5 | 4–5 | 5 | 4–5 | 5 | 2 | 0 | 2 | 0 |
| 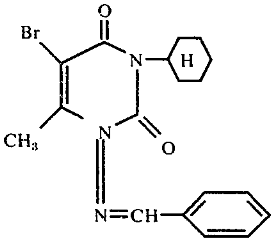 | 5 | 4 | 5 | 5 | 5 | 0 | 2 | 1 | 0 |
| | 2.5 | 4 | 5 | 5 | 5 | 0 | 1 | 0 | 0 |
| 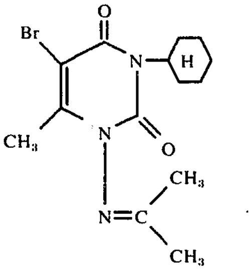 | 5 | 5 | 5 | 5 | 5 | 1 | 0 | 1 | 0 |
| | 2.5 | 4–5 | 5 | 5 | 5 | 0 | 0 | O | 0 |
| 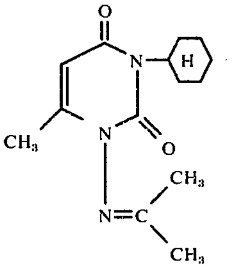 | 5 | 3 | 5 | 5 | 5 | 3 | 2 | 2 | 0 |
| | 2.5 | 3 | 4–5 | 4–5 | 5 | 3 | 1 | 0 | 0 |
| 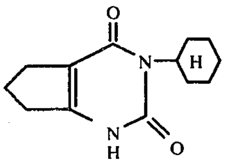 | 5 | 5 | 5 | 4 | 5 | 4–5 | 1 | 3 | 2 |
| | 2.5 | 5 | 5 | 3 | 5 | 4 | 0 | 2 | 2 |
| | (known) | | | | | | | | |

EXAMPLE B

Post-emergence Test

Solvent: 5 parts by weight of acetone

Emulsifier: 1 part by weight of alkylaryl polyglycol ether

To produce a suitable preparation of active compound, 1 part by weight of active compound was mixed with the stated amount of solvent, the stated amount of emulsifier was added and the concentrate was then diluted with water to the desired concentration.

Test plants which had a height of 5–15 cm were sprayed with the preparation of the active compound in such a way that the amounts of active compound per unit area indicated in the table were applied. Depending on the concentration of the spray liquor, the amount of water used was between 1,000 and 2,000 l/ha. After three weeks, the degree of damage to the plants was determined and characterized by the values 0–5, which had the following meaning:

0—no effect
1—a few slightly burned spots
2—marked damage to leaves
3—some leaves and parts of stalks partially dead
4—plant partially destroyed
5—plant completely dead The active compounds, the amounts used and the results can be seen from the table which follows:

Table III
| Post-emergence Test | | | | | | | | | | | |
|---|---|---|---|---|---|---|---|---|---|---|---|
| Active compound | Amount of active compound used, kg/ha | Echinochloa | Chenopodium | Sinapis | Galinsoga | Stellaria | Urtica | Oats | Cotton | Wheat | Carrots |
| 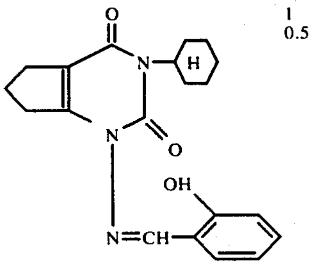 | 1 | 4 | 3 | 5 | 5 | 4 | 5 | 2 | 1 | 2 | 0 |
| | 0.5 | 3 | 2 | 5 | 2 | 2 | 2 | 0 | 0 | 2 | 0 |
| 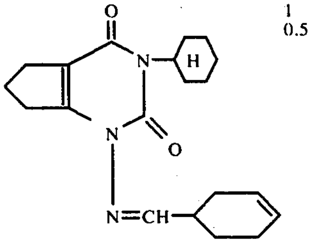 | 1 | 4 | 5 | 5 | 5 | 5 | 4 | 3 | 3 | 3 | 0 |
| | 0.5 | 3 | 4 | 5 | 3 | 3 | 3 | 2 | 3 | 3 | 0 |
| 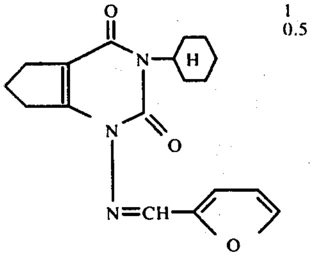 | 1 | 5 | 4 | 5 | 5 | 5 | 4 | 1 | 1 | 3 | 1 |
| | 0.5 | 4 | 3 | 5 | 4 | 3 | 3 | 0 | 0 | 2 | 0 |
| 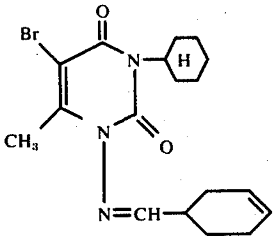 | 1 | 5 | 5 | 5 | 5 | 5 | 5 | 4 | 2 | 4 | 1 |
| | 0.5 | 5 | 5 | 5 | 4 | 4 | 3 | 3 | 0 | 3 | 0 |
| 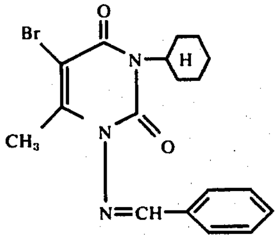 | 1 | 5 | 5 | 5 | 5 | 5 | 4 | 3 | 3 | 3 | 2 |
| | 0.5 | 4–5 | 5 | 5 | 5 | 4 | 3 | 3 | 2 | 3 | 0 |
| 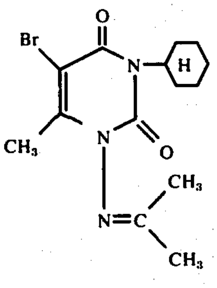 | 1 | 5 | 5 | 5 | 5 | 5 | 5 | 4 | 5 | 3 | 4 |
| | 0.5 | 5 | 5 | 5 | 5 | 5 | 5 | 3 | 2 | 3 | 2 |

Table III-continued

| Post-emergence Test | | | | | | | | | | | |
|---|---|---|---|---|---|---|---|---|---|---|---|
| Active compound | Amount of active compound used, kg/ha | Echinochloa | Chenopodium | Sinapis | Galinsoga | Stellaria | Urtica | Oats | Cotton | Wheat | Carrots |
| 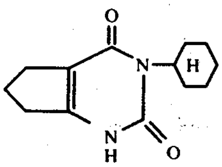 (known) | 1 | 5 | 1 | 5 | 3 | 4 | 3 | 2 | 1 | 3 | 3 |
| | 0.5 | 4 | 0 | 4–5 | 2 | 2 | 2 | 1 | 0 | 2 | 2 |

It will be understood that the specification and examples are illustrative but not limitative of the present invention and that other embodiments within the spirit and scope of the invention will suggest themselves to those skilled in the art.

What is claimed is:

1. 1-Alkylideneaminouracil compound of the formula

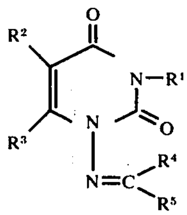

(I)

wherein $R^1$ is alkyl or substituted alkyl of up to 12 carbon atoms wherein the substitutent is selected from up to 3 members of the group consisting of halogen, nitrile or alkoxy of from 1 to 3 carbon atoms; or alkenyl and alkynyl of from 3 to 12 carbon atoms; cycloalkyl, cycloalkyl-alkyl of from 5 to 7 carbon atoms; mono-, di-, or tri-halo-cycloalkyl and alkylcycloalkyl of from 5 to 8 carbon atoms in the cycloalkyl moiety and up to 3 carbon atoms in the alkyl moiety; alkoxycycloalkyl of from 5 to 8 carbon atoms; alkoxycarbonylalkyl of from 1 to 4 carbon atoms in the alkoxy moiety and 1 to 2 carbon atoms in the alkyl moiety; alkylthioalkyl or alkoxyalkyl of from 1 to 4 carbon atoms in the alkoxy or alkylthio moiety and 1 to 6 carbon atoms in the alkyl moiety; aralkyl and substituted aralkyl of 6 or 10 carbon atoms in the aryl moiety and 1 or 2 carbon atoms in the alkyl part wherein the substitutents are selected from up to 3 members of the group consisting of halogen, alkyl of 1 to 4 carbon atoms, and haloalkyl of from 1 to 2 carbon atoms and 2 to 5 halogen atoms, $R^2$ is hydrogen or halogen; and $R^3$ is methyl or $R^2$ and $R^3$ together represent an alkylene bridge of from 3 to 5 carbon atoms, which forms, with the two adjacent carbon atoms, a 5- to 7-membered ring and which is optionally mono-substituted by alkyl of from 1 to 3 carbon atoms;

$R^4$ is alkyl of from 1 to 6 carbon atoms, cycloalkyl or cycloalkenyl of from 5 to 7 carbon atoms or aryl of from 6 or 10 carbon atoms aryl substituted one to three times with substituents selected from halogen, alkyl, haloalkyl and haloalkoxy of up to 5 carbon atoms, alkoxy, alkylthio and alkylsulfonyl of up to 3 carbon atoms, hydroxyl, and nitro; or $R^4$ is a 5-membered or 6-membered heterocyclic containing the hetero-atoms O, N or S selected from 2-furyl, 2-thienyl and 2-pyridinyl which may be substituted with substituents selected from halogen, haloalkyl and haloalkoxy, of up to 5 carbon atoms, alkoxy, alkylthio and alkylsulfonyl of up to 3 carbon atoms, hydroxyl, and nitro; and $R^5$ is hydrogen, alkyl of from 1 to 6 carbon atoms, or unsubstituted or substituted aryl of from 6 or 10 carbon atoms where the substitutents are selected from up to 3 members of the group consisting of halogen, haloalkyl and haloalkoxy of up to 5 carbon atoms, alkoxy, alkylthio and alkylsulfonyl of up to 3 carbon atoms, hydroxyl and nitro.

2. 1-Alkylideneaminouracil compound as claimed in claim 1 wherein $R^1$ is alkyl or substituted alkyl of up to 12 carbon atoms.

3. 1-Alkylideneaminouracil compound as claimed in claim 1 wherein $R^1$ is alkenyl or alkynyl of up to 12 carbon atoms.

4. 1-Alkylideneaminouracil compound as claimed in claim 1 wherein $R^1$ is cycloalkyl, alkylcycloalkyl, cycloalkylalkyl or halocycloalkyl of up to 11 carbon atoms.

5. 1-Alkylideneaminouracil compound as claimed in claim 1 wherein $R^1$ is alkoxycarbonylalkyl of up to 10 carbon atoms.

6. 1-Alkylideneaminouracil compound as claimed in claim 1 wherein $R^1$ is alkylthioalkyl or alkoxyalkyl of up to 10 carbon atoms.

7. 1-Alkylideneaminouracil compound as claimed in claim 1 wherein $R^1$ is aralkyl of up to 12 carbon atoms.

8. 1-Alkylideneaminouracil compound as claimed in claim 1 wherein $R^1$ is substituted aralkyl wherein the substituent is on the aryl portion of the moiety and is selected from up to 3 members of the group consisting of halogen, haloalkyl of from 2 to 5 halogen atoms and from 1 to 2 carbon atoms, and alkyl of from 1 to 4 carbon atoms.

9. 1-Alkylideneaminouracil compound as claimed in claim 1 wherein $R^2$ is hydrogen.

10. 1-Alkylideneaminouracil compound as claimed in claim 1 wherein $R^2$ is halogen.

11. 1-Alkylideneaminouracil compound as claimed in claim 1 wherein $R^3$ is hydrogen.

12. 1-Alkylideneaminouracil compound as claimed in claim 1 wherein $R^3$ is alkyl of up to 4 carbon atoms.

13. 1-Alkylideneaminouracil compound as claimed in claim 1 wherein $R^2$ and $R^3$ taken together represent an alkylene bridge of from 3 to 5 carbon atoms to form a ring structure which may be optionally mono substituted with alkyl of from 1 to 3 carbon atoms.

14. 1-Alkylideneaminouracil compound as claimed in claim 1 wherein $R^4$ is alkyl of from 1 to 6 carbon atoms.

15. 1-Alkylideneaminouracil compound as claimed in claim 1 wherein $R^4$ is cycloalkyl or cycloalkenyl of from 5 to 7 carbon atoms in the ring.

16. 1-Alkylideneaminouracil compound as claimed in claim 1 wherein $R^4$ is aryl of up to 10 carbon atoms.

17. 1-Alkylideneaminouracil compound as claimed in claim 1 wherein $R^4$ is substituted aryl of up to 10 carbon atoms in the aryl moiety wherein the substituent is at least one and up to 3 of halogen, haloalkyl or haloalkoxy of up to 5 carbon atoms, alkyl of up to 4 carbon atoms, alkoxyalkylthio or alkylsulfonyl of up to 3 carbon atoms, hydroxy and nitro.

18. 1-Alkylideneaminouracil compound as claimed in claim 1 wherein $R^4$ is a 5- or 6-ring member heterocyclic structure including at least one oxygen, nitrogen or sulfur as the hetero atom.

19. 1-Alkylideneaminouracil compound as claimed in claim 1 wherein $R^4$ is a substituted 5- or 6-ring member heterocyclic structure having at least one oxygen, nitrogen or sulfur atom in said ring wherein the substituent is at least one and up to 3 of halogen, haloalkyl or haloalkoxy of up to 5 carbon atoms, alkyl of up to 4 carbon atoms, alkoxyalkylthio or alkylsulfonyl of up to 3 carbon atoms, hydroxy and nitro.

20. 1-Alkylideneaminouracil compound as claimed in claim 1 wherein $R^4$ is 2-furyl.

21. 1-Alkylideneaminouracil compound as claimed in claim 1 wherein $R^4$ is 2-pyridinyl, 22. 1-Alkylideneaminouracil compound as claimed in claim 1 wherein $R^4$ is 2-thienyl.

23. 1-Alkylideneaminouracil compound as claimed in claim 1 wherein $R^5$ is hydrogen.

24. 1-Alkylideneaminouracil compound as claimed in claim 1 wherein $R^5$ is alkyl of up to 6 carbon atoms.

25. 1-Alkylideneaminouracil compound as claimed in claim 1 wherein $R^5$ is aryl of up to 10 carbon atoms.

26. 1-Alkylideneaminouracil compound as claimed in claim 1 wherein $R^5$ is substituted aryl of up to 10 carbon atoms in the aryl moiety wherein the substituent is at least one and up to 3 of halogen, haloalkyl or haloalkoxy of up to 5 carbon atoms, alkyl of up to 4 carbon atoms, alkoxyalkylthio or alkylsulfonyl of up to 3 carbon atoms, hydroxy and nitro.

27. 1-Alkylideneaminouracil compound as claimed in claim 1 designated 1-furfurylideneamino-3-cyclohexyl-5,6-trimethylene-uracil.

28. 1-Alkylideneaminouracil compound as claimed in claim 1 designated 1-(3,4-dichlorobenzylideneamino)-3-cyclohexyl-5-bromo-6-methyl-uracil.

29. 1-Alkylideneaminouracil compound as claimed in claim 1 designated 1-benzylideneamino-3-cyclohexyl-5-bromo-6-methyl-uracil.

30. 1-Alkylideneaminouracil compound as claimed in claim 1 designated 1-[(cyclohex-3-en-1-yl)-methylidenamino]-3-cyclohexyl-5-bromo-6-methyl-uracil.

31. 1-Alkylideneaminouracil compound of the formula

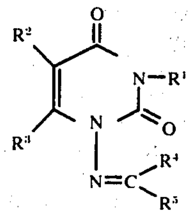

(I)

wherein $R^1$ is alkyl or mono-, di-, tri-, halo-alkyl of from 1 to 12 carbon atoms; allyl; cycloalkyl of from 5 to 7 carbon atoms; cycloalkylalkyl of from 5 to 8 carbon atoms in the cycloalkyl moiety and 1 to 2 carbon atoms in the alkyl moiety, alkylcycloalkyl of from 5 to 8 carbon atoms in the alkyl moiety; phenylalkyl and halophenylalkyl of from 1 to 2 carbon atoms in the alkyl moiety;

$R^2$ is hydrogen, chlorine or bromine;

$R^3$ is methyl;

$R^2$ and $R^3$ together represent a 3-membered alkylene bridge which is optionally substituted by methyl;

$R^4$ is methyl, cyclohexyl; cyclohex-3-en-yl; phenyl, which is optionally substituted one to three times by halogen, haloalkyl or haloalkoxy of 1 to 2 carbon atoms and 2 to 5 halogen atoms, alkyl or alkoxy of from 1 to 4 carbon atoms; hydroxy and nitro; or $R^4$ is a 5-membered or 6-membered heterocyclic containing the hetero-atoms O, N or S selected from 2-furyl, 2-thienyl and 2-pyridinyl, and $R^5$ is hydrogen or methyl.

32. 1-Alkylideneaminouracil compound as claimed in claim 31 wherein $R^4$ is selected from 2-furyl, 2-thienyl and 2-pyridinyl.

33. Herbicidal composition comprising a herbicidally acceptable carrier and in effective amounts a 1-alkylideneaminouracil compound as claimed in claim 1.

34. Method for combating undesired vegetation, which method comprises applying to such vegetation or its habitat herbicidally effective amounts of a 1-alkylideneaminouracil compound of the formula

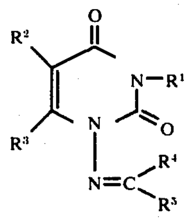

(I)

wherein $R^1$ is alkyl or substituted alkyl of up to 12 carbon atoms wherein the substitutent is selected from up to 3 members of the group consisting of halogen, nitrile or alkoxy of from 1 to 3 carbon atoms;

or alkenyl and alkynyl of from 3 to 12 carbon atoms; cycloalkyl, cycloalkyl-alkyl of from 5 to 7 carbon atoms; mono-, di-, or tri-halo-cycloalkyl and alkylcycloalkyl of from 5 to 8 carbon atoms in the cycloalkyl moiety and up to 3 carbon atoms in the alkyl moiety; alkoxycycloalkyl of from 5 to 8 carbon atoms; alkoxycarbonylalkyl of from 1 to 4 carbon atoms in the alkoxy moiety and 1 to 2 carbon atoms in the alkyl moiety;

alkylthioalkyl or alkoxyalkyl of from 1 to 4 carbon atoms in the alkoxy or alkylthio moiety and 1 to 6 carbon atoms in the alkyl moiety;

aralkyl and substituted aralkyl of 6 or 10 carbon atoms in the aryl moiety and 1 or 2 carbon atoms in the alkyl part wherein the substitutents are selected from up to 3 members of the group consisting of halogen, alkyl of 1 to 4 carbon atoms, and haloalkyl of from 1 to 2 carbon atoms and 2 to 5 halogen atoms, $R^2$ is hydrogen or halogen; and $R^3$ methyl or $R^2$ and $R^3$ together represent an alkylene bridge of from 3 to 5 carbon atoms, which forms, with the two adjacent carbon atoms, a 5- to 7-membered ring and which is optionally mono-substituted by alkyl of from 1 to 3 carbon atoms;

$R^4$ is alkyl of from 1 to 6 carbon atoms, cycloalkyl or cycloalkenyl of from 5 to 7 carbon atoms or aryl of from 6 or 10 carbon atoms aryl substituted one to three times with substituents selected from halogen, alkyl, haloalkyl and haloalkoxy of up to 5 carbon atoms, alkoxy, alkylthio and alkylsulfonyl of up to 3 carbon atoms, hydroxyl, and nitro; or $R^4$ is a 5-membered or 6-membered heterocyclic containing the hetero-atoms O, N or S selected from 2-furyl, 2-thienyl and 2-pyridinyl which may be substituted with substituents selected from halogen, haloalkyl and haloalkoxy, of up to 5 carbon atoms, alkoxy, alkylthio and alkysulfonyl of up to 3 carbon atoms, hydroxyl, and nitro; and $R^5$ is hydrogen, alkyl of from 1 to 6 carbon atoms, or unsubstituted or substituted aryl of from 6 or 10 carbon atoms where the substituents are selected from up to 3 members of the group consisting of halogen, haloalkyl and haloalkoxy of up to 5 carbon atoms, alkoxy, alkylthio and alkylsulfonyl of up to 3 carbon atoms, hydroxyl and nitro.

35. Method as claimed in claim 34 wherein said compound is applied to weeds growing in a crop cultivation in such manner as to cause substantial damage to the weeds without substantial injury to the crops.

36. Method as claimed in claim 35 wherein said crop is a cereal crop.

37. Method as claimed in claim 36 wherein said cereal crop is corn.

38. Method as claimed in claim 35 wherein said crop is cotton.

39. Method as claimed in claim 34 wherein said compound is 1-furfurylideneamino-3-cyclohexyl-5,6-trimethyleneuracil.

40. Method as claimed in claim 34 wherein said compound is 1-(3,4-dichlorobenzylideneamino)-3-cyclohexyl-5-bromo-6-methyl-uracil.

41. Method as claimed in claim 34 wherein said compound is 1-benzylideneamino-3-cyclohexyl-5-bromo-6-methyl-uracil.

42. Method as claimed in claim 34 wherein said compound is 1-(cyclohex-3-en-1-yl)-3-cyclohexyl-5-bromo-6-methyl-uracil.

* * * * *